United States Patent [19]

Mizuno et al.

[11] Patent Number: 5,019,615
[45] Date of Patent: May 28, 1991

[54] POLYPHENYLENE ETHER/POLYESTER BLEND WITH NITRODIAMINE COMPOUND

[75] Inventors: Yukio Mizuno, Ehime; Takashi Maruyama, Shinichi; Shinichi Yachigo, Osaka, all of Japan

[73] Assignee: Sumitomo Chemical Company, Ltd., Osaka, Japan

[21] Appl. No.: 504,808

[22] Filed: Apr. 5, 1990

[30] Foreign Application Priority Data

Apr. 6, 1989 [JP] Japan ........................ 88361

[51] Int. Cl.$^5$ ................ C08K 5/3462; C08K 5/32
[52] U.S. Cl. ..................... 524/100; 524/108; 524/260
[58] Field of Search ............... 524/100, 260, 108

[56] References Cited

U.S. PATENT DOCUMENTS

| | | | |
|---|---|---|---|
| Re. 19,654 | 7/1935 | Reed | 524/100 |
| 1,970,972 | 8/1935 | Orthner et al. | 524/260 |
| 3,221,080 | 11/1965 | Fox | 260/860 |
| 3,247,162 | 4/1966 | Newland et al. | 524/260 |
| 3,679,622 | 7/1972 | Grier | 524/100 |
| 4,614,773 | 9/1986 | Sugio et al. | |
| 4,806,297 | 2/1989 | Brown et al. | |
| 4,848,814 | 7/1989 | Suzuki et al. | |
| 4,849,785 | 7/1989 | Tanabe | |
| 4,866,130 | 9/1989 | Brown et al. | |

FOREIGN PATENT DOCUMENTS

| | | |
|---|---|---|
| 148774 | 7/1985 | European Pat. Off. |
| 0253365 | 1/1988 | European Pat. Off. |
| 49-98858 | 9/1974 | Japan |
| 51-21664 | 7/1976 | Japan |
| 60-221459 | 11/1985 | Japan |
| 62-260855 | 11/1987 | Japan |
| 43-17812 | 7/1988 | Japan |
| 87/00850 | 2/1987 | PCT Int'l Appl. |

OTHER PUBLICATIONS

110 Chem. Abs. (No. 6), Abs. No. 40362r (Feb. 6, 1989).
111 Chem. Abs. (No. 24), Abs. No. 215844z (Dec. 11, 1989).
112 Chem. Abs. (No. 12), Abs. No. 100475h (Mar. 19,1990).

Primary Examiner—Veronica P. Hoke
Attorney, Agent, or Firm—Cushman, Darby & Cushman

[57] ABSTRACT

The present resin composition is improved in compatibility between thermoplastic polyester and polyphenylene ether and is excellent in processability, solvent resistance, and impact strength.

This resin composition comprises:
100 parts by weight of a composition comprising
(A) 5–95 % by weight of a polyphenylene ether resin and
(B) 95–5 % by weight of a thermoplastic polyester and
0–100 parts by weight based on said composition comprising (A) and (B) of a rubber-like polymer, and
0.01–10 parts by weight based on said composition comprising (A) and (B), of (D) a compound comprising dinitrodiamine represented by the formula (I):

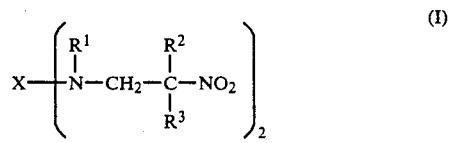

wherein X represents a divalent chain aliphatic, cycloaliphatic or aromatic group which may contain halogen or oxygen, $R^1$ represents a hydrogen atom, a chain aliphatic group, a cycloaliphatic group or an aromatic group and when X and $R^1$ are both chain aliphatic groups, the nitrogen atoms may further link through $R^1$ to each other, $R^2$ and $R^3$ each represents a hydrogen atom or an alkyl group of 1–12 carbon atoms and $R^2$ and $R^3$ may link to each other to form a ring.

10 Claims, No Drawings

POLYPHENYLENE ETHER/POLYESTER BLEND WITH NITRODIAMINE COMPOUND

The present invention relates to a resin composition which comprises a polyphenylene ether resin and a thermoplastic polyester.

More particularly, it relates to a novel resin composition which comprises a resin composition comprising a thermoplastic polyester and a polyphenylene ether resin comprising at least one member selected from a polyphenylene ether, a modified polyphenylene ether, a composition containing a polyphenylene ether and a composition containing a modified polyphenylene ether, to which are added a compound comprising a dinitrodiamine, and, if necessary, a rubber-like polymer. This resin composition is excellent in solvent resistance, flowability, mechanical properties and processability.

The composition of the present invention can be made into shaped articles, sheets, or films by injection molding, extrusion molding, etc.

Polyphenylene ether is superior in mechanical properties, electrical properties, and heat resistance, and besides in dimensional stability and is noticed as a resin suitable for various uses, but it is inferior in processability, impact strength and solvent resistance, for example, against chemicals such as gasoline.

In order to improve processability and impact strength, Japanese Patent Publication (Kokoku) No. 43-17812 and Japanese Patent Publication (Kokai) No. 49-98858 have proposed blends of polyphenylene ether with polystyrene or rubber-reinforced polystyrene. However, these resin compositions are also inferior in solvent resistance.

Resin compositions comprising rubber-reinforced polystyrene/polyphenylene ether has excellent impact strength and processability and are industrially mass-produced. However, they are limited in their uses due to their inferior solvent resistance.

Further, Japanese Patent Publication (Kokoku) No. 42-15872 has proposed to add aromatic polycarbonate. However, although resin compositions comprising aromatic polycarbonate/polyphenylene ether are improved to some extent in processability without severe damage of heat resistance of polyphenylene ether, this improvement is not sufficient due to relatively high melt viscosity of aromatic polycarbonate and besides, solvent resistance is hardly improved.

Further, Japanese Patent Publication (Kokoku) No. 51-21664 has proposed to add polyester in order to improve processability and solvent resistance of polyphenylene ether. However, polyphenylene ether and polyester are very poor in compatibility with each other and the resulting resin composition is inferior in mechanical properties. Especially, it is quite inferior when content of polyester exceeds 20%. Furthermore, molded articles obtained therefrom by injection molding show delamination phenomenon and good molded articles cannot be obtained.

As methods to improve these defects, Japanese Patent Publication (Kokai) No. 60-221459 has proposed to add a copolymer of a monomer of unsaturated compound having an epoxy group and styrene, Japanese Patent Publication (Kokai) No. 62-260855 has proposed to add maleic anhydride, Japanese Patent Publication (Kokaki) No. 62-263251 has proposed to add a copolymer of styrene and unsaturated carboxylic acid, and Japanese Patent Publication (Kohyo) No. 63-500387 has proposed to add at least one polymer containing aromatic polycarbonate unit or a blend of this polymer with styrene homopolymer. However, these methods are still unsatisfactory.

The inventors have already found a resin composition excellent in mechanical properties and solvent resistance and good in processability and well balanced in properties which comprises a polyphenylene ether, a thermoplastic polyester resin and an amino resin, and have filed a patent application therefor (Japanese Patent Application No. 63-165376). However, this resin composition is still unsatisfactory in mechanical properties in practical use.

The principal object of the present invention is to provide a practically usable resin composition which is improved in compatibility between polyphenylene ether and thermoplastic polyester and which is excellent in solvent resistance as well as heat resistance and impact strength.

As a result of intensive research conducted by the inventors in an attempt to develop a technique effective to improve a resin composition comprising polyphenylene ether and thermoplastic polyester, it has been found that a resin composition excellent in solvent resistence, mechanical properties, heat resistance, and processability can be obtained by adding a compound comprising a dinitrodiamine and, if necessary, a rubber-like polymer to a resin composition comprising a thermoplastic polyester and a polyphenylene ether resin comprising at least one member selected from a polyphenylene ether, a modified polyphenylene ether modified with a polyfunctional compound, an epoxy compound or an organosilane compound, a composition containing a polyphenylene ether and a composition containing the above modified polyphenylene ether.

That is, the present invention relates to a resin composition which comprises:
100 parts by weight of a composition comprising
(A) 5–95% by weight of a polyphenylene ether resin and
(B) 95–5% by weight of a thermoplastic polyester,
(C) a rubber-like polymer in an amount of 0–100 parts by weight based on 100 parts by weight of the composition comprising the above components (A) and (B), and
(D) a compound comprising a dinitrodiamine represented by the formula (I):

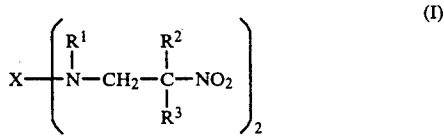

(wherein X represents a divalent chain aliphatic, cycloaliphatic or aromatic group which may contain halogen or oxygen, $R^1$ represents a hydrogen atom, a chain aliphatic group, a cycloaliphatic group or an aromatic group and when X and $R^1$ are both chain aliphatic groups, the nitrogen atoms may further link to each other through $R^1$, and $R^2$ and $R^3$ each independently represents a hydrogen atom or an alkyl group of 1–12 carbon atoms and $R^2$ and $R^3$ may link to each other to form a ring) in an amount of 0.01–10 parts by weight based on 100 parts by weight of the composition comprising the above components (A) and (B).

The present invention further relates to a resin composition which comprises the abovementioned resin composition to which is added (M) an aromatic vinyl polymer, a copolymer of an aromatic vinyl compound and another monomer or a rubber-modified aromatic vinyl polymer.

The polyphenylene ether resin (A) is at least one resin selected from a polyphenylene ether, a modified polyphenylene ether, a composition containing a polyphenylene ether and a composition containing a modified polyphenylene ether.

The modified polyphenylene ether includes polyphenylene ethers modified with (E) a polyfunctional compound, (J) an epoxy compound, (K) an organosilane compound, or the like.

The polyphenylene ether is a polymer obtained by oxidation polymerization of a phenol compound represented by the formula (II):

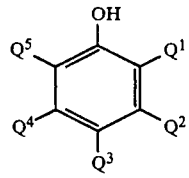

(wherein $Q^1$, $Q^2$, $Q^3$, $Q^4$ and $Q^5$ each represents a hydrogen atom, a halogen atom, a hydrocarbon residue or a substituted hydrocarbon residue and one of them is a hydrogen atom) with oxygen or a gas containing oxygen using an oxidation coupling catalyst.

Examples of $Q^1$, $Q^2$, $Q^3$, $Q^4$ and $Q^5$ in the above formula (II) are hydrogen atom, chlorine atom, fluorine atom, bromine atom, iodine atom, methyl group, ethyl group, propyl group, butyl group, chloroethyl group, hydroxyethyl group, phenylethyl group, benzyl group, hydroxymethyl group, carboxyethyl group, methoxycarbonylethyl group, cyanoethyl group, phenyl group, chlorophenyl group, methylphenyl group, dimethylphenyl group, and ethylphenyl group.

Preferred examples of the phenol compounds shown by the above frormula are phenol, o-, m- or p-cresol, 2,6-, 2,5-, 2,4- or 3,5-dimethylphenol, 2-methyl-6-phenylphenol, 2,6-diphenylphenol, 2,6-diethylphenol, 2-methyl-6-ethylphenol, and 2,3,5-, 2,3,6-, or 2,4,6-trimethylphenol. These phenol compounds may be used singly or in combination of two or more.

Further, the polyphenylene ether may be copolymers of the phenol compounds of the above formula and other phenol compounds, for example, dihydric phenols such as bisphenol A, tetrabromobisphenol A, resorcin, and hydroquinone. Among them, especially preferred are homopolymers and copolymers of 2,6-dimethylphenol or 2,3,6-trimethylphenol.

Any oxidation coupling catalysts can be used for oxidation polymerization of the phenol compounds as far as they have polymerization ability. Typical examples thereof are catalysts comprising cuprous salt and tert. amine such as cuprous chloride/trimethylamine, cuprous acetate/triethylamine and cuprous chloride/pyridine; catalysts comprising cupric salt/tert. amine and alkali metal hydroxide such as cupric chloride/pyridine/potassium hydroxide; catalysts comprising manganese salt and/primary amine such as manganese chloride/ ethanolamine and manganese acetate/ethylenediamine; catalysts comprising manganese salt and alcoholate or phenolate such as manganese chloride/sodium methylate and manganese chloride/sodium phenolate; catalysts comprising manganese salt, alkali hydroxide and amine such as manganese chloride/NaOH/ diethanolamine/dibutylamine, manganese chloride/ NaOH/triethanolamine/dibutylamine and manganese chloride/NaOH/monoethanolamine/dibutylamine, and catalysts comprising cobalt salt and tert. amine.

Intrinsic viscosity (measured in chloroform at 30° C.) of the polyphenylene ether used in the present invention has no special limitation, but preferably is 0.2–1.0 dl/g, more preferably 0.25–0.6 dl/g and optimum intrinsic viscosity can be selected depending on circumstances.

Polyfunctional compounds (E) used as modifiers for polyphenylene ether in the present invention are those which have in their molecule at least one of carboxylic acid group, acid anhydride group, acid amide group, imide group, carboxylic acid ester group, epoxy group, amino group and hydroxyl group. Preferred are compounds (F) which have in their molecule both (a) carbon-carbon double bond or carbon-carbon triple bond and (b) at least one of carboxylic acid group, acid anhydride group, acid amide group, imide group, carboxylic acid ester group, epoxy group, amino group and hydroxyl group.

Examples of the compounds (F) are maleic anhydride, maleic acid, fumaric acid, maleimide, maleic acid hydrazide, reaction products of maleic anhydride and diamine, for example, compounds having the structures:

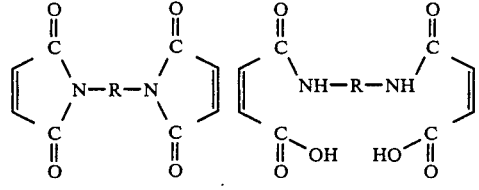

(wherein R is an aliphatic or aromatic group), methylnadic anhydride, dichloromaleic anhydride, maleic acid amide, natural fats and oils such as soybean oil, tung oil, caster oil, linseed oil, hempseed oil, cottonseed oil, sesame oil, rapeseed oil, peanut oil, camellia oil, olive oil, coconut oil and sardine oil; epoxidized natural fats and oils such as epoxidized soybean oil; unsaturated carboxylic acids such as acrylic acid, butenoic acid, crotonic acid, vinylacetic acid, methacrylic acid, pentenoic acid, angelic acid, tiglic acid, 2-pentenoic acid, 3-pentenoic acid, α-ethylacrylic acid, β-methylcrotonic acid, 4-pentenoic acid, 2-hexenoic acid, 2-methyl-2-pentenoic acid, 3-methyl-2-pentenoic acid, α-ethylcrotonic acid, 2,2-dimethyl-3'-butenoic acid, 2-heptenoic acid, 2-octenoic acid, 4-decenoic acid, 9-undecenoic acid, 10-undecenoic acid, 4-dodecenoic acid, 5-dodecenoic acid, 4-tetradecenoic acid, 9-tetradecenoic acid, 9-hexadecenoic acid, 2-octadecenoic acid, 9-octadecenoic acid, eicosenoic acid, docosenoic acid, erucic acid, tetracocenoic acid, mycolipenic acid, 2,4-pentadienoic acid, 2,4-hexadienoic acid, diallylacetic acid, geranic acid, 2,4-decadienoic acid, 2,4-dodecadienoic acid, 9,12-hexadecadienoic acid, 9,12-octadecadienoic acid, hexadecatrienoic acid, linolic acid, linolenic acid, octadecatrienoic acid, eicosadienoic acid, eicosatrienoic acid, eicosatetraenoic acid, ricinoleic acid, eleosteric acid, oleic acid, eicosapentaenoic acid, erucinic acid, docosadienoic acid, docosatrienoic acid, docosatetraenoic acid, docosapentaenoic acid, tetracosenoic acid, hexacosenoic acid, hexacodienoic acid, octacosenoic acid, and triacontenoic acid; and esters, acid amides and anhydrides of these unsaturated carboxylic acids; unsaturated alcohols such as allyl alcohol, crotyl alcohol, methylvinyl carbinol, allyl carbinol, methylpropenyl carbinol, 4-pentene-1-ol, 10-undecene-1-ol, propargyl alcohol, 1,4-pentadiene-3-ol, 1,4-hexadiene-3-ol, 3,5-hexadiene-2-ol, 2,4-hexadiene-1-ol, alcohols represented by the formulas $C_nH_{2n-5}OH$, $C_nH_{2n-7}OH$, $C_nH_{2n-9}OH$ (n is a positive integer), 3-butene-1,2-diol, 2,5-dimethyl-3-hexene-2,5-diol, 1,5-hexadiene-3,4-diol, and 2,6-octadiene-4,5-diol and unsaturated amines such as ones where an OH group of these unsaturated alcohols is replaced by an —NH₂ group, low polymers (e.g., those of about 500—about 10000 in average molecular weight) or high polymers (e.g., those of at least 10000 in average molecular weight) such as of butadiene and isoprene to which maleic anhydride or a phenol is added or into which amino group, carboxylic acid group, hydroxyl group, epoxy group or the like is introduced.

Other preferred polyfunctional compounds (E) are compounds (G) selected from aliphatic carboxylic acids, acid esters thereof and acid amides thereof represented by the formula:

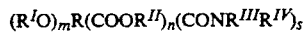

(wherein R represents a straight chain or branched chain saturated aliphatic hydrocarbon group of 2–20 carbon atoms, $R^I$ each independently represents a hydrogen atom, or an alkyl, aryl, acyl, or carbonyldioxy group of 1–10 carbon atoms, $R^{II}$ each independently represents a hydrogen atom or an alkyl or aryl group of 1–20 carbon atoms, $R^{III}$ and $R^{IV}$ each independently represents a hydrogen atom or an alkyl or aryl group of 1–10 carbon atoms, and m, n, and s are 0 or integers of 1 or more with $m+n+s \geq 2$) and derivatives thereof.

As example of compounds (G), mention may be made of hydroxyacetic acid, lactic acid, α-hydroxy-n-butyric acid, α-hydroxyisobutyric acid, α-hydroxy-n-valeric acid, α-hydroxyisovaleric acid, 2-hydroxy-2-methylbutanoic acid, α-hydroxy-n-caproic acid, α-hydroxyisocaproic acid, 2-ethyl-2-hydroxybutanoic acid, 2-hydroxy-3,3-dimethylbutanoic acid, 2-hydroxy-2-methylpentanoic acid, 2-hydroxy-5-methylhexanoic acid, 2-hydroxy-2,4-dimethylpentanoic acid, 3-hydroxypropionic acid, β-hydroxybutyric acid, β-hydroxyisobutyric acid, β-hydroxy-n-valeric acid, β-hydroxyisovaleric acid, 2-hydroxymethylbutanoic acid, hydroxypivalic acid, 3-hydroxy-2-methylpentanoic acid, 1,1-hydroxytetradecanoic acid, jalapinolic acid, 1,4-hydroxyhexadecanoic acid, sabinic acid, juniperic acid, hydroxymalonic acid, methyltartronic acid, ethyltartronic acid, n-propyltartronic acid, isopropyltartronic acid, hydroxymethylmalonic acid, hydroxyisopropylmalonic acid, ethyl-hydroxymethylmalonic acid, malic acid, α-methylmalic acid, α-hydroxy-α'-methylsuccinic acid, α-hydroxy-α,α'-dimethylsuccinic acid, α-hydroxy-α,α'-diethylsuccinic acid, α-hydroxy-α'-ethylsuccinic acid, α-hydroxy-α'-methyl-α-ethylsuccinic acid, trimethylmalic acid, α-hydroxyglutaric acid, β-hydroxyglutaric acid, β-hydroxy-β-methylglutaric acid, α-hydroxyadipic acid, citric acid, isocitric acid, norcaperatic acid, agaricic acid, glyceric acid, α,β-dihydroxybutyric acid, α,β-dihydroxyisobutyric acid, β,β'-dihydroxyisobutyric acid, β,γ-dihydroxybutyric acid, α,γ-dihydroxy-β,β-dimethylbutyric acid, α,β-dihydroxy-α-isopropylbutyric acid, ipuroic acid, ustilic acid-A, 9,10-dihydroxyoctadecanoic acid, tartaric acid (optically active body or racemic body), mesotartaric acid, methyltartaric acid, α,β-dihydroxyglutaric acid, α,γ-dihydroxyglutaric acid, α,γ-dihydroxy-β-methylglutaric acid, α,γ-dihydroxy-β-methyl-β-ethylglutaric acid, α,γ-dihydroxy-α,γ-dimethylglutaric acid, α,δ-dihydroxyadipic acid, β-γ-dihydroxyadipic acid, 6,7-dihydroxydodecanoic diacid, 7,8-dihydroxyhexadecanoic diacid, furoionic acid, trihydroxybutyric acid, trihydroxyisobutyric acid, trihydroxyglutaric acid, succinic acid, glutaric acid, adipic acid, α-methylglutaric acid, and dodecanoic diacid.

Furthermore, the derivatives of the above formula include lactones, acid anhydrides, alkali metal salts, alkaline earth metal salts, and salts with amines. As examples thereof, mention may be made of β-propiolactone, glycollide, lactide, β-methylpropiolactone, β,β-dimethylpropiolactone, β-n-propylpropiolactone, β-isopropylpropiolactone, β-methyl-β-ethylpropiolactone, γ-butyrolactone, γ-valerolactone, δ-valerolactone, δ-caprolactone, ε-caprolactone, 1,5-hydroxypentadecanoic acid lactone, γ-butyrolactone-α-carboxylic acid, paraconic acid, α-methylparaconic acid, β-methylparaconic acid, α-ethylparaconic acid, α-isopropylparaconic acid, γ-methylparaconic acid, γ-ethylparaconic acid, α,γ-dimethylparaconic acid, β,γ-dimethylparaconic acid, α,α,β-trimethylparaconic acid, γ,γ-dimethylparaconic acid, nephrosteraic acid, γ-valerolactone-γ-carboxylic acid, γ-isopropyl-γ-butyrolactone-γ-carboxylic acid, α,α-dimethyl-γ-butyrolactone-γ-carboxylic acid, β-methyl-γ-valerolactone-γ-carboxylic acid, α,β-dimethyl-γ-valerolactone-γ-carboxylic acid, α, β-dimethyl-γ-butyrolactone-γ-carboxylic acid, homoisocarpic acid, α-(γ-oxycarbonylpropyl)-γ-butyrolactone, β-hydroxyadipic acid-γ-lactone, α,δ-dimethyl-β-hydroxyadipic acid-γ-lactone, β-hydroxy-β-methyladipic acid-γ-lactone, α-(δ'-carboxy-n-butyl)-γ-butylolactone, α-methylisocitric acid lactone, cinchonic acid, α-hydroxy-γ-butyrolactone, β-hydroxy-γ-butyrolactone, δ-hydroxy-γ-valerolactone, pantolactone, mevalonic acid, malic anhydride, tartaric anhydride, hydroxyglutaric anhydride, α,β,γ-trihydroxyvaleric acid lactone, α-hydroxy-α-hydroxymethyl-γ-butyrolactone, succinic anhydride, and glutaric anhydride. These may be used singly or in combination of two or more.

Among them, especially preferred are tartaric acid, malic acid, citric acid, and derivatives thereof. These include acids in various commercially available forms such as anhydride or hydrate. Examples of useful derivatives are acetyl citrate, monostearyl or distearyl citrate, N,N'-diethylcitric acid amide, N,N'-dipropylcitric acid amide, N-phenylcitric acid amide, N-dodecylcitric acid amide, N,N'-didodecylcitric acid amide, N-dodecylcitric acid amide, calcium malate, calcium citrate, potassium malate and potassium citrate.

As other preferred polyfunctional compounds (E), mention may be made of compounds (H) which have in their molecule both (a) acid halide group, preferably acid chloride group and (b) at least one of carboxylic acid group, acid anhydride group, carboxylic acid ester group and acid amide group, preferably carboxylic acid group and carboxylic anhydride group.

As examples of compounds (H), mention may be made of anhydrotrimellitic acid chloride, chloroformylcitric anhydride, chloroformylcitric acid, chloroformylglutaric anhydride, chloroformylglutaric acid, chloroacetylcitric anhydride, chloroacetylcitric acid, trimellitic acid chloride, and chloroacetylglutaric acid. Anhydrotrimellitic acid chloride is especially preferred.

These compounds (F), (G) and (H) are mentioned in detail in U.S. Pat. Nos. 4,315,086 and 4,642,358, which are incorporated by reference herein.

Epoxy compound (J) used as a modifier in the present invention is an epoxy compound comprising a compound having oxirane group in its molecule and/or a condensation polymer of a dihydric phenol and epichlorohydrin.

Examples of epoxy compound (J) include epoxides of olefins or cycloalkenes such as ethylene oxide, propylene oxide and cyclohexene oxide. They further include condensates of a dihydric phenol and epichlorohydrin at various ratios and typical examples thereof are condensates of bisphenol A and epichlorohydrin such as commercially available SUMIEPOXY ® ELA-115, ELA-127, ELA-128, ELA-134, ESA-011, ESA-014, ESA-017, and ESA-019 manufactured by Sumitomo Chemical Co., Ltd. and phenoxy resins of Union Carbide Corp., condensates of resorcin and epichlorohydrin, condensates of hydroquinone and epichlorohydrin, condensates of tetrabromobisphenol A and epichlorohydrin, and glycidyl etherification products of phenol novolak or cresol novolak such as a product line of SUMIEPOXY ® ESCN220 manufactured by Sumitomo Chemical Co., Ltd.

Further included are condensates of polyhydric alcohol and epichlorohydrin and typical examples of the polyhydric alcohols are ethylene glycol, propylene glycol, butylene glycol, polyethylene glycol, polypropylene glycol, glycerine, trimethylolethane, trimethylolpropane and pentaerythritol.

Further examples are glycidyl etherification products of monohydric phenols or monohydric alcohols such as phenylglycidyl ether, butylglycidyl ether and cresylglycidyl ether.

Further, mention may be made of glycidylation products of amine compounds such as commercially available SUMIEPOXY ® ELM-120, which is a diglycidylation product of aniline, commercially supplied by Sumitomo Chemical Co. Ltd.

Furthermore, there may be used polymers of epoxy-containing unsaturated compounds such as glycidyl acrylate, glycidyl methacrylate and allyl glycidyl ether, and copolymers of epoxy-containing unsaturated compound and at least one of other monomers such as ethylene, propylene, butene, styrene, α-methylstyrene, 4-methyl-pentene, chlorostyrene, bromostyrene, acrylic acid, acrylic acid esters, acrylonitrile, vinyl chloride, methacrylic acid, methacrylic acid esters, maleic anhydride, and vinyl acetate. Of these polymers, especially preferred are styrene-glycidyl (meth)acrylate copolymer and ethylene-glycidyl (meth)acrylate copolymer.

Organosilane compound (K) used in the present invention is an organosilane compound which has in its molecule simultaneously (a) at least one silicon atom which bonds to a carbon atom through an oxygen atom, (b) carbon-carbon double bond or carbon-carbon triple bond, and (c) at least one functional group selected from amino group, mercapto group, carboxylic acid group, acid anhydride group, acid amide group, carboxylic acid ester group, imide group and hydroxyl group.

In these compounds (K), C-O-Si component is usually present as alkoxy group or acetoxy group which directly bonds to silicon atom. Such alkoxy group or acetoxy group generally has less than 15 carbon atoms and may contain a hetero-atom such as oxygen. Further, in these compounds, two or more silicon atoms may be present. When two or more silicon atoms are present, these are bonded through oxygen bond (e.g., in case of siloxane), silicon-silicon bond, or bifunctional organic group such as methylene group and phenylene group.

Examples of suitable organosilane compounds (K) are γ-aminopropyltriethoxysilane, 2-(3-cyclohexenyl)ethyltrimethoxysilane, 1,3-divinyltetraethoxysilane, vinyltris(2-methoxyethoxy)silane, 5-bicycloheptenyltriethoxysilane and γ-mercaptopropyltrimethoxysilane.

Amount of compounds (E), (F), (G), (H), (J) and (K) can be variously selected depending on object, but is generally 200 parts by weight or less, preferably 80 parts by weight or less, more preferably 20 parts by weight or less, and most preferably 0.01-10 parts by weight per 100 parts by weight of polyphenylene ether.

In modification of polyphenylene ether with the above-mentioned compounds (E), (F), (G), (H), (J) and (K), radical initiators may be used. The radical initiators include known organic peroxides and diazo compounds such as benzoyl peroxide, dicumyl peroxide, di-tert-butyl peroxide, tert-butylcumyl peroxide, tert-butyl hydroperoxide, cumene hydroperoxide and azobisisobutyronitrile. Amount of the radical initiator is 0.01-10 parts by weight, preferably 0.1-5 parts by weight per 100 parts by weight of polyphenylene ether.

With reference to the modified polyphenylene ether, it may be a chemical reaction product of the above compound with polyphenylene ether or the above compound and polyphenylene ether may be combined through physical interaction such as physical adsorption of the compound to polyphenylene ether.

Furthermore, as preferable modified polyphenylene ether, mention may be made of polymers obtained by grafting an unsaturated monomer other than the above-mentioned polyfunctional compound (F) having unsaturated group of the above-mentioned polyfunctional compound (F) having unsaturated group and other unsaturated monomer on polyphenylene ether in the presence of radical initiators.

The unsaturated monomers are preferably vinyl and-/or vinylidene compounds and the like (L). Examples of these compounds (L) are as follows: Aromatic vinyl or vinylidene compounds such as α-methylstyrene, o-, m- and p-methylstyrene, chlorostyrene, bromostyrene, divinylbenzene, hydroxystyrene and aminostyrene; olefins such as ethylene; (meth)acrylic acid ester compounds such as methyl (meth)acrylate, ethyl (meth)acrylate, propyl (meth)acrylate, and octyl (meth)acrylate; cyanovinyl compounds such as acrylonitrile and methacrylonitrile; vinyl ester compounds such as vinyl acetate; vinyl ether compounds such as methylvinyl ether, ethylvinyl ether and butylvinyl ether; and unsaturated halogen compounds such as vinyl chloride and vinylidene chloride These may be used singly or in combination of two or more. These unsaturated monomers to be grafted are preferably styrene, styrene-glycidyl methacrylate, styrene-glycidyl acrylate, styrene-maleic anhydride, styrene-acrylic acid and styrenemethacrylic acid.

Amount of compound (L) is 200 parts by weight or less, preferably 0.5-100 parts by weight, more preferably 1-50 parts by weight per 100 parts by weight of polyphenylene ether.

Method for production of the modified polyphenylene ether in the present invention is not limitative and known methods can be employed. Examples of the methods are as follows:

(1) Polyphenylene ether and the above compound in the form of pellet, powder, fine piece, etc. are uniformly mixed by a high-speed stirrer and then melt kneaded.

(2) The above compound is added to a solution in which polyphenylene ether is dissolved or swollen to dissolve or swell the compound, followed by heating with stirring.

(3) The above compound is added to polyphenylene ether and the mixture is dispersed in water and heated with stirring.

In the above case, it is preferred to use dispersion stabilizers such as polyvinyl alcohol, sodium dodecylbenzenesulfonate, and calcium phosphate. In some case, a solvent which dissolves or swells polyphenylene ether may be added.

In the method (1), there are no limitations in temperature and time for melt kneading. The kneading temperature is generally 150°-350° C., though it may somewhat change depending on kind and amount of the compound. Any apparatus can be used for melt kneading as far as it can handle a molten viscous material, and either of batch or continuous method can he used. Examples of apparatus used for these methods are single-screw or multi-screw extruders, Banbury mixers, rolls, kneaders, etc.

Solvents used for the above-mentioned methods (2) and (3) have no special limitation and any solvents which can dissolve or swell polyphenylene ether may be used.

Examples of these solvents are chloroform, methylene chloride, benzene, xylene, chlorobenzene, cyclohexane, styrene, toluene, and o-chlorophenol. Mixed solvents which can dissolve or swell polyphenylene ether may also be used. There are no limitations in temperature and time for mixing and in general, the temperature may be 20°-250° C. and the time is 1 minute-10 hours.

When modified polyphenylene ether is used in the present invention, it is preferred to produce the resin composition by previously preparing the modified polyphenylene ether and then mixing it with other components, but it is also possible to produce the resin composition by simultaneously mixing the compound as modifier, polyphenylene ether and other components.

The composition containing polyphenylene ether or modified polyphenylene ether used in the present invention means a composition containing polyphenylene ether or modified polyphenylene ether and (M) an aromatic vinyl polymer, a copolymer of an aromatic vinyl compound with other monomer or a rubber-modified aromatic vinyl polymer mentioned later.

Thermoplastic polyester (B) is obtained by polycondensation of a dicarboxylic acid or its functional derivative and a dihydroxy compound or its functional derivative.

As examples of the dicarboxylic acid, mention may be made of aromatic dicarboxylic acids such as terephthalic acid, isophthalic acid, and 2,6-naphthalenedicarboxylic acid; nuclear-substituted aromatic dicarboxylic acids in which a hydrogen atom of the aromatic nucleus of the above aromatic dicarboxylic acid is substituted with methyl group, ethyl group, phenyl group or the like; aliphatic dicarboxylic acids having 2-20 carbon atoms such as adipic acid, sebacic acid and dodecanedicarboxylic acid; and alicyclic dicarboxylic acids such as cyclohexanedicarboxylic acid.

The functional derivatives of dicarboxylic acids include acid chlorides and esters such as carboxylic acid methyl esters and phenyl esters of the above-mentioned compounds.

Examples of the dihydroxy compounds are aliphatic diols and alicyclic diols such as ethylene glycol, 1,3-propanediol, 1,4-butanediol, 1,6-hexanediol, 1,10-decanediol, 1,4-cyclohexanediol and cyclohexanedimethanol and dihydric phenols represented by the following formula (III):

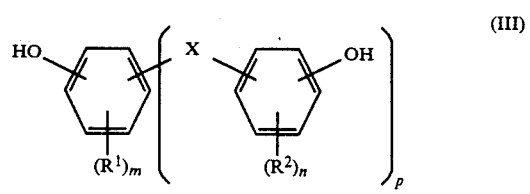

(wherein X represents a substituted or unsubstituted alkylene group of 1-20 carbon atoms, an alkylidene group of 1-10 carbon atoms, a cycloalkylene group of 4-8 carbon atoms, —O—, —S—, or —$SO_2$—, or the benzene nuclei directly link to each other, $R^1$ and $R^2$ each represents a halogen atom or an alkyl group of 1-12 carbon atoms, m and n each represents an integer of 0-4 and p represents 0 or 1). Examples of these dihydric phenols are bisphenol A, bis-(4-hydroxyphenyl)-methane, bis-(4-hydroxy-3-methylphenyl)-propane, 2,2-bis-(3',5'-dibromo-4'-hydroxyphenyl)-propane, 1,1-bis(4-hydroxyphenyl)-1-phenyl-ethane, bis(4-hydroxyphenyl)-diphenylmethane, 1,1-bis-(4'-hydroxyphenyl)-cyclohexane, resorcin, hydroquinone, 4,4'-dihydroxydiphenyl, bis-(4-hydroxyphenyl)-sulfone and methyl-nuclear-substituted derivatives thereof.

Typical examples of the functional derivatives of dihydroxy compounds are diacetate derivatives.

The above compounds may be used singly or in combination of two or more. Moreover, copolymers of these compounds with p-hydroxybenzoic acid or polyethylene glycol may also be used.

Among these thermoplastic polyesters, preferred are polyethylene terephthalate, polybutylene terephthalate and modified polymers containing these structures such as copolymers with polyethers such as polyethylene glycol and polypropylene glycol.

Intrinsic viscosity of polyethylene terephthalate or polybutylene terephthalate is not critical, but preferably 0.5-2.5 dl/g and optimum intrinsic viscosity can be chosen depending on circumstances.

Mixing ratio of the polyphenylene ether resin (A) and the thermoplastic polyester (B) is the polyphenylene ether resin: 5-95% by weight and the thermoplastic polyester: 95-5% by weight. If amount of thermoplastic polyester is less than 5% by weight, effect to improve solvent resistance is small and if it is more than 95% by weight, thermal properties such as heat distortion temperature tend to deteriorate.

Compound (D) comprising a dinitrodiamine which plays the most important role in improving compatibility between polyphenylene ether resin (A) and thermoplastic polyester (B) in the composition of the present invention is represented by the formula (I):

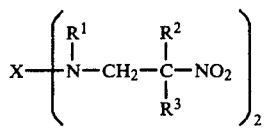 (I)

(wherein X represents a divalent chain aliphatic group, cycloaliphatic group or aromatic group which may contain halogen or oxygen, R¹ represents a hydrogen atom, a chain aliphatic group, a cycloaliphatic group or an aromatic group, when both the X and R¹ are chain aliphatic groups, the nitrogen atoms may further link to each other through R¹, and R² and R³ each independently represents a hydrogen atom or an alkyl group of 1-12 carbon atoms and R² and R³ may link to each other to form a ring).

The dinitrodiamines represented by the above formula (I) can be easily produced by condensation reaction of a diamine, a nitroalkane and formaldehyde as starting materials in an inert solvent such as methanol. A small amount of an alkaline compound may be used as a catalyst to accelerate the reaction.

As examples of the compounds comprising these dinitrodiamines, mention may be made of the following compounds (1)–(48) wherein —Z represents

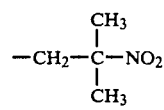

 (1)

 (2)

 (3)

 (4)

 (5)

 (6)

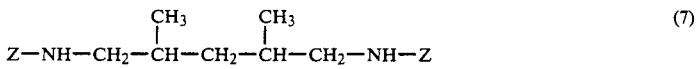 (7)

 (8)

 (9)

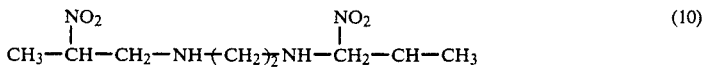 (10)

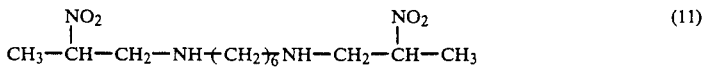 (11)

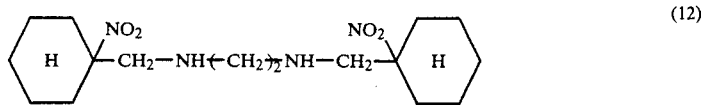 (12)

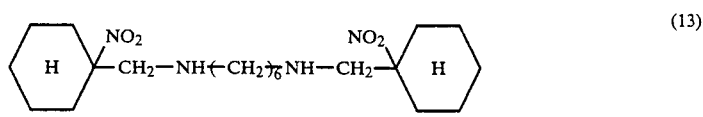 (13)

 (14)

 (15)

 (16)

-continued
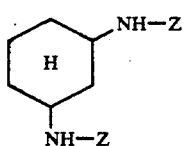 (17)
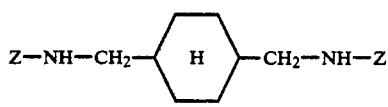 (18)
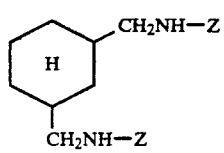 (19)
 (20)
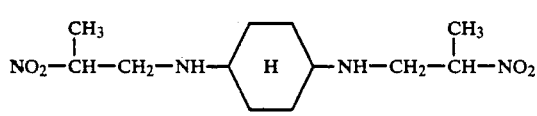 (21)
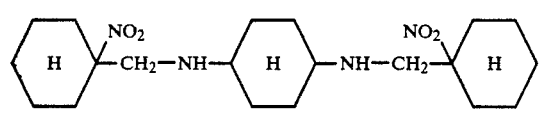 (22)
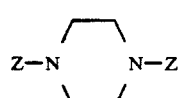 (23)
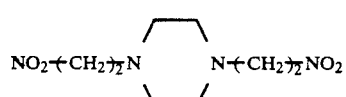 (24)
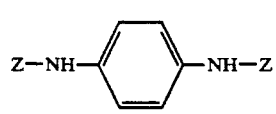 (25)
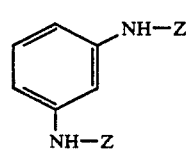 (26)
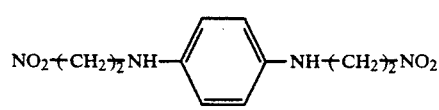 (27)
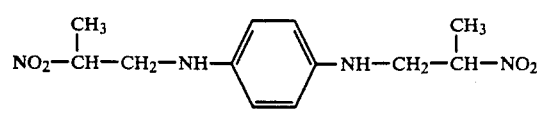 (28)

-continued
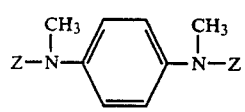
(29)
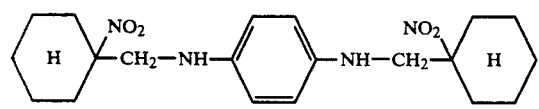
(30)
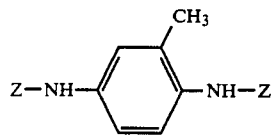
(31)
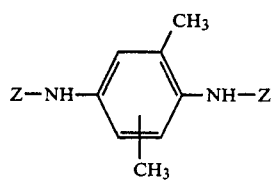
(32)
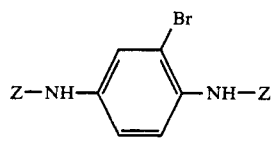
(33)
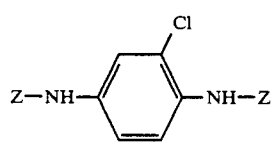
(34)
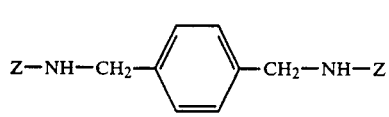
(35)
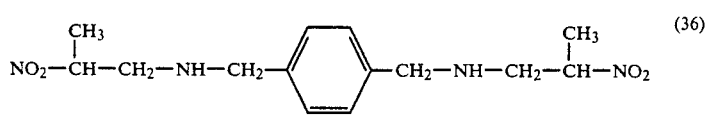
(36)
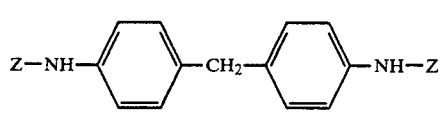
(37)
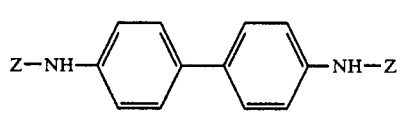
(38)
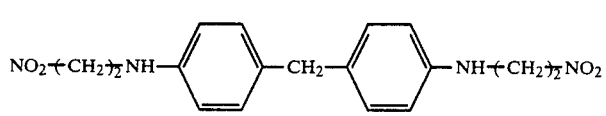
(39)
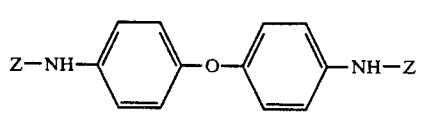
(40)

-continued

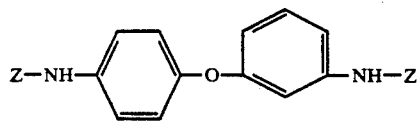 (41)

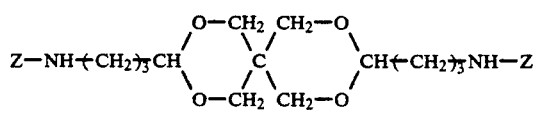 (42)

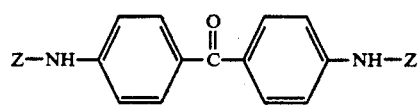 (43)

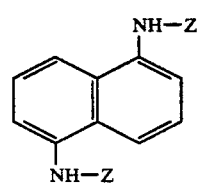 (44)

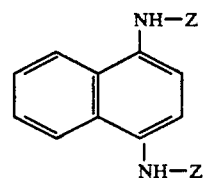 (45)

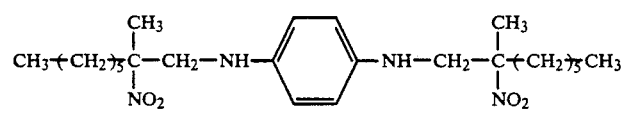 (46)

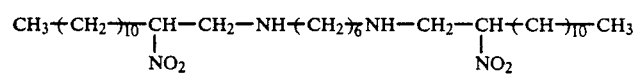 (47)

(48)

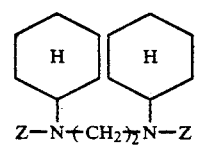

As mentioned above, substituent X in the formula (I) is a divalent chain aliphatic group, cycloaliphatic group or aromatic group. As in the above compounds (33) and (34), the substituent X may contain halogen and as in the above compounds (40)–(43), the substituent X may contain oxygen. Among these compounds, preferred are those of the formula (I) in which X is a chain aliphatic group, especially chain aliphatic group of 4–12 carbon atoms.

$R^1$ in the formula (I) is a hydrogen atom, a chain aliphatic group, a cycloaliphatic group or an aromatic group. When X and $R^1$ are both chain aliphatic groups, the compounds include those of the formula (I) in which nitrogen atoms per se further link through $R^1$ and a ring is formed by X, $R^1$ and two nitrogen atoms like compounds (23) and (24).

Furthermore, $R^2$ and $R^3$ in the formula (I) may be identical or different and each represents a hydrogen atom or an alkyl group of 1–12 carbon atoms. The compounds (D) further include those of the formula (I) wherein $R^2$ and $R^3$ link to each other to form a ring like compounds (12), (13), (22) and (30).

Compound (D) comprising a dinitrodiamine may be a single compound, a mixture of two or more compounds, a mixture with fillers such as silica and talc as referred to later or a mixture with other additives. Thus, the compound (D) may be used in any of these forms.

Amount of compound (D) comprising a dinitrodiamine is 0.01–10 parts by weight, preferably 0.1–5 parts by weight based on 100 parts by weight of a composition comprising polyphenylene ether resin (A) and thermoplastic polyester (B). If amount of compound (D) is less than 0.01 part by weight, the effect for improvement aimed at by the present invention is small and if it is more than 10 parts by weight, no more advantage is obtained but rather not economical.

In order to remarkably increase impact strength, it is preferred to add rubber-like polymer (C) as an impact strength modifier.

The rubber-like polymer (C) used in the present invention means natural and synthetic polymer which is elastic at room temperature, for example, 20°–25° C. Examples of the rubber-like polymer (C) are natural rubber, diene rubbers such as polybutadiene, polyisoprene, and polychloroprene and copolymers of diene and vinyl monomer such as styrene-butadiene random copolymer, styrene-butadiene block copolymer, styrene-butadiene-styrene block copolymer, styrene-isoprene random copolymer, styrene-isoprene block copolymer, styrene-isoprene-styrene block copolymer, styrene-grafted polybutadiene, and butadiene-acrylonitrile copolymer, polyisobutylene and copolymers of isobutylene and butadiene or isoprene, ethylene-propylene copolymer and ethylene-propylene-non-conjugated diene copolymer, ethylene-butene-1 copolymer, ethylene-acrylic acid copolymer and alkali metal salts thereof so-called ionomers, ethylene-glycidyl acrylate copolymer, ethylene-alkyl acrylate copolymer such as ethylene-ethyl acrylate copolymer and ethylene-butyl acrylate copolymer, thiokol rubber, polysulfide rubber, acrylic rubber, polyurethane rubber, polyether rubber, epichlorohydrin rubber, polyester elastomers and polyamide elastomer.

These rubber-like polymers can be produced by various processes such as emulsion polymerization and solution polymerization and using various catalysts such as peroxides, trialkylaluminum, lithium halides and nickel based catalysts.

Furthermore, the rubber-like polymer may be one which has various crosslinking degrees, various proportions of micro structures such as cis structure, trans structure and vinyl group or various average particle sizes of rubber in the resin composition.

Various copolymers such as random copolymers, block copolymers, and graft copolymers may be used as the rubber-like polymers of the present invention.

The rubber-like polymers may copolymerized with other monomers such as other olefins, dienes, aromatic vinyl compounds, acrylic acid, acrylic acid esters, and methacrylic acid esters at the time of preparation of the rubber-like polymers. Methods for copolymerization may be any methods such as random copolymerization, block copolymerization and graft copolymerization. As examples of these monomers, mention may be made of ethylene, propylene, styrene, chlorostyrene, α-methylstyrene, butadiene, isoprene, chlorobutadiene, butene-1, isobutylene, methyl acrylate, acrylic acid, ethyl acrylate, butyl acrylate, glycidyl acrylate, methyl methacrylate, acrylonitrile, maleic anhydride, and glycidyl methacrylate.

Furthermore, the rubber-like polymers include various modified polymers. Examples thereof are hydroxy- or carboxy-terminal-modified polybutadienes, partially or completely hydrogenated styrene-butadiene, styrene-butadiene-styrene, styrene-isoprene or styrene-isoprene-styrene block copolymers, rubber-like polymers modified with at least one compound selected from compounds having in its molecule at least one of carboxy group, amino group, imino group, epoxy group, amide group, vinyl group, isocyanate group and hydroxyl group, acid anhydrides, carboxylic acid esters and oxazoline ring, for example, ethylene-propylene copolymer, ethylene-propylene-non-conjugated diene copolymer, styrene-butadiene copolymer including A - B or A - B - A' block, random or graft copolymer, hydrogenated copolymer thereof, styrene-isoprene copolymer including A - B or A - B - A' block, random or graft copolymer and hydrogenated copolymer thereof which are modified with acrylic acid, himic anhydride, glycidyl methacrylate or maleic anhydride. The modification can be performed by known methods such as graft copolymerization and random copolymerization. One or two or more of these rubber-like polymers may be used.

In addition, diene rubbers and copolymers of diene and vinyl compound different in micro structure of double bond such as vinyl group, cis-1,4-bond and trans 1,4-bond may also be used as the rubber-like polymers of the present invention.

Preferred rubber-like polymers include copolymers comprising 40–100% by weight of butadiene and 60–0% by weight of styrene, copolymers comprising 35–82% by weight of butadiene and 35–18% by weight of acrylonitrile, styrene-butadiene and styrene-butadiene-styrene block copolymers including all of linear block copolymers, radial block copolymers, etc. and hydrogenated products thereof, styrene-isoprene and styrene-isoprene-styrene block copolymers and hydrogenated products thereof, styrene-grafted polybutadiene obtained by adding styrene to polybutadiene or butadiene-styrene copolymer latex and emulsion polymerizing it by radical initiator, ethylene-propylene copolymer and ethylene-propylene-non-conjugated diene copolymer and these polymers modified with maleic anhydride, glycidyl methacrylate or styrene.

The rubber-like polymer (C) is used in an amount of 0–100 parts by weight, preferably 50 parts by weight or less and more preferably 30 parts by weight or less per 100 parts by weight of the composition comprising polyphenylene ether resin (A) and thermoplastic polyester (B).

In practice of the present invention, it is also possible to add other polymers and auxiliaries to the resin composition of the present invention. These other polymers include, for example, polyolefins such as polyethylene, polypropylene, ethylenepropylene block copolymer, polymethylpentene, ethylene-α-olefin copolymers such as ethylenebutene copolymer, ethylene-4-methyl-pentene copolymer and ethylene-hexene copolymer which have a density of 0.90–0.97 g/cm$^3$; homopolymers and copolymers of various vinyl compounds such as polyvinyl chloride, polymethyl methacrylate, polyvinyl acetate, polyvinylpyridine, polyvinylcarbazole, polyacrylamide, polyacrylonitrile, ethylenevinyl acetate copolymer and aromatic vinyl polymers; polysulfones, polyether sulfones, polyphenylene sulfide; polyamides such as 6-nylon, 6,6-nylon and 12-nylon; condensation-polymerized compounds such as polyacetal; and various thermosetting resins such as silicone resin, fluororesin, polyimide, polyamideimide, phenol resin, alkyd resin, unsaturated polyester resin, epoxy resin, and Dapon resin.

Among the above-mentioned other polymers, preferred are polyolefins, polyamides, and (M) aromatic vinyl polymers, copolymers of aromatic vinyl compounds and other monomers and rubber modified aromatic vinyl polymers.

(M) aromatic vinyl polymers, copolymers of aromatic vinyl compounds with other monomers or rubber modified aromatic vinyl polymers are selected from those which have at least 25% by weight of polymer unit derived from a monomer having the following formula:

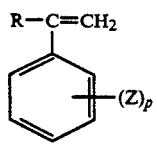

wherein R represents a hydrogen atom, a lower alkyl group such as an alkyl group of 1-4 carbon atoms or a halogen atom, Z represents a hydrogen atom, a vinyl group, a halogen atom, an amino group, a hydroxyl group or a lower alkyl group, and p represents 0 or an integer of 1-5.

As examples of aromatic vinyl polymers and copolymers of aromatic vinyl compounds and other monomers, mention may be made of homopolymers such as polystyrene, polychlorostyrene, and poly-α-methylstyrene and copolymers thereof, and styrene-containing copolymers such as styreneacrylonitrile copolymer, styrene-maleic anhydride copolymer, styrene-glycidyl methacrylate copolymer, styrene-acrylic acid copolymer, styrene-N-phenylmaleimide copolymer, styrene-divinylbenzene copolymer, and styrene-acrylonitrile-α-methylstyrene copolymer. Among these polymers, preferred are polystyrene, styrene-α-methylstyrene copolymer, styrene-acrylonitrile copolymer, styrene-α-chlorostyrene copolymer, styrene-methyl methacrylate copolymer, styrene-glycidyl methacrylate copolymer, styrene-maleic anhydride copolymer and styreneacrylic acid copolymer.

The rubber modified aromatic vinyl polymers are those which comprise aromatic vinyl polymer or copolymer matrix in which rubber particles are dispersed to form a two-phase system. They can be produced by mechanical mixing of the abovementioned rubber-like polymer (C) with aromatic vinyl polymer or copolymer or by dissolving rubber in aromatic vinyl compound monomer, followed by polymerization of the aromatic vinyl compound monomer. According to the latter method, so-called high-impact polystyrenes such as styrene-butadiene rubber-modified polystyrene, ethylene-propylene rubber-modified polystyrene and polybutadiene rubber-modified polystyrene are industrially produced.

These polymers may be previously mixed with polyphenylene ether resin or thermoplastic polyester as component (A) or component (B) or polyphenylene ether may be modified with the compounds as modifier in the presence of these polymers. Furthermore, it is also possible to simultaneously mix or react the polyphenylene ether resin (A), thermoplastic polyester (B), compounds (E)-(K) as modifier, rubber-like polymer (C), compound (D) comprising a dinitrodiamine and the above polymer. Other sequences of mixing may also be employed.

As the auxiliaries which can be added to the resin composition of the present invention, mention may be made of, for example, reinforcing materials such as glass fiber, carbon fiber, potassium titanate fiber, and high-modulus polyamide fiber, inorganic and organic fillers such as carbon black, silica, TiO$_2$, talc, calcium carbonate, magnesium sulfate, and wollastonite, plasticizers such as triphenyl phosphate and phthalic acid esters, lubricants, stabilizers, flame retardants such as Sb$_2$O$_3$, halogen compounds and phosphoric acid esters, dyes and pigments.

The method for producing the resin composition of the present invention is not limitative and any known methods can be used.

A method in which the components are mixed in the form of solutions and solvents are evaporated or in which said mixture is precipitated in a nonsolvent, is effective. However, from industrial viewpoint, a method of kneading them in molten state is employed in practice. The melt kneading is carried out using such a kneading machine as generally used single-screw or twin-screw extruder and various kneaders. A twin-screw kneader is especially preferred.

Before kneading, it is preferred to uniformly blend respective resin components in the form of powder or pellet by using such a mixer as a tumbler or a Henschel mixer. However, each resin may be separately fed directly to a kneading apparatus through a metering device without the blending.

The kneaded resin composition can be molded by injection, extrusion or various other molding processes. The present invention further includes a method in which molded articles are obtained by dry-blending the components firstly at the time of injection molding or extrusion molding and then directly kneading the components during its operation of melt processing, without the previous kneading.

There is no special limitation in sequence of kneading of the components. Respective components may be kneaded at the same time or polyphenylene ether resin (A) and compound (D) comprising a dinitrodiamine may be previously kneaded to obtain a composition and then rubber-like polymer (C) and thermoplastic polyester (B) may be kneaded with the composition, that is, respective components in molten state can be kneaded at two or more steps. Further, using a kneading machine having two or more introduction openings, components (A), (C) and (D) may be simultaneously introduced from the introduction opening of upperstream side and component (B) may be introduced from opening of downstream side. Other sequences of kneading may also be employed.

The following examples are merely illustrative of the present invention and the present invention is not restricted to these examples. In the examples, deflection temperature under load (H.D.T.) and Izod impact strength (thickness: 3.2 mm) were measured according to JIS K7207 and JIS K7110, respectively.

REFERENCE EXAMPLE 1

Preparation of compound (D) comprising a dinitrodiamine (i) In a one-liter four-necked flask equipped with a stirrer, a thermometer and a condenser was charged 156.8 g (1.76 mol) of 2-nitropropane and thereto were added 200 ml of methanol as a solvent and 16.7 g (0.04 mol) of 40% methanolic solution of trimethylbenzylammonium hydroxide as a catalyst. This mixture was heated to 50° C. and kept at that temperature and then thereto was added dropwise 136.3 g (1.68 mol) of 37% formalin over about 1 hour. Thereafter, the reaction mass was heated to 60° C. and thereto was added dropwise a solution of 86.5 g (0.8 mol) of p-phenylenediamine in 500 ml of methanol at 40° C. over about 1 hour. After completion of addition, the reaction mass was kept at 60° C. for about 4 hours to precipitate crystal to form a slurry of the reaction mass.

This reaction mass was gradually cooled to 5° C. and then was filtrated to collect precipitated crystal. The crystal was washed with methanol and water and vacuum dried at lower than 50° C. to obtain 226.3 g of N,N'-bis(2-methyl-2-nitropropyl)-1,4-diaminobenzene (yield based on p-phenylenediamine: 91.1%). The resulting compound was light yellow crystal and had a melting point of 135°-137° C. This compound is referred to as compound (a).

Results of elementary analysis of this compound were as follows:

|  | C | H | N |
|---|---|---|---|
| Found | 54.13% | 7.22% | 18.09% |
| Calcd. | 54.18% | 7.14% | 18.05% |

Furthermore, it was confirmed from FD-MASS, NMR spectrum and IR spectrum that this compound had a structure represented by the following formula:

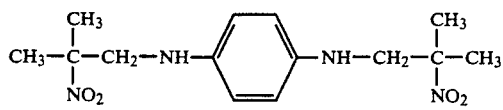

Dinitrodiamines shown in Table 1 were prepared in the same manner as above except that strating material was changed.

TABLE 1

| Compound | Name of compound |
|---|---|
| (b) | N,N'-bis(2-nitropropyl)-1,3-diaminobenzene |
| (c) | N,N'-bis(2-methyl-2-nitropropyl)-4,4'-diaminodiphenylmethane |
| (d) | N,N'-bis(1-nitrocyclohexylmethyl)-4,4'-diaminodiphenyl ether |
| (e) | N,N'-bis(2-methyl-2-nitrooctyl)-1,4-diaminobenzene |

(ii) In a one-liter four-necked flask equipped with a stirrer, a thermometer and a condenser were charged 16.2 g (1.0 mol) of 1,6-diaminohexane, 178.2 g (2.0 mol) of 2-nitropropane, and 140 g of methanol and then, under stirring thereto was added dropwise 162.3 g (2.0 mol) of 37% formalin at 45°-55° C. over one hour. After completion of addition of formalin, the mixture was kept at that temperature for one hour and then 200 ml of water was added thereto to carry out liquid-separation.

Oil layer was washed with 200 ml of water and then concentrated at 60° C. under 30 Torr to obtain 304 g of light yellow liquid. This liquid was subjected to high performance liquid chromatography to find that it contained 298 g of N,N'-bis(2-methyl-2-nitropropyl)-1,6-diaminohexane and 5 g of 2-nitropropane.

To this liquid were added 300 ml of n-hexane and 150 ml of toluene to dissolve the liquid and then the liquid was cooled to 5° C. to precipitate crystal to form a slurry. This mixture was filtrated and the resulting crystal was washed with 100 ml of cold n-hexane and vacuum dried at lower than 20° C. to obtain 288 g of N,N'-bis(2-methyl-2-nitropropyl)-1,6-diaminohexane. This compound was light yellow crystal and had a melting point of 26°-27° C. This compound is referred to as compound (f).

Elementary analysis values of this compound were as follows:

|  | C | H | N |
|---|---|---|---|
| Found | 52.69% | 9.45% | 17.57% |
| Calcd. | 52.81% | 9.50% | 17.60% |

Dinitrodiamines shown in Table 2 were prepared in the same manner as above except that starting material was changed.

TABLE 2

| Compound | Name of compound |
|---|---|
| (g) | N,N'-bis(2-methyl-2-nitropropyl)-1,2-diaminoethane |
| (h) | N,N'-bis(2-methyl-2-nitropropyl)-1,12-diaminododecane |
| (i) | N,N'-bis(2-methyl-2-nitropropyl)-1,18-diaminooctadecane |
| (j) | N,N'-bis(2-nitropropyl)-1,6-diaminohexane |
| (k) | N,N'-bis(2-methyl-2-nitropropyl)-1,4-bis(aminomethyl)cyclohexane |
| (l) | N,N'-bis(2-methyl-2-nitropropyl)piperazine |

EXAMPLE 1

50 g of maleic anhydride and 10 g of dicumyl peroxide were added to 5 kg of poly-2,6-dimethylphenylene ether having an intrinsic viscosity of 0.43 dl/g measured in chloroform at 25° C. and these were mixed by Henschel mixer. The mixture was then melt kneaded by a twin-screw extruder at 300°-320° C. and pelletized to obtain maleic anhydride-modified polyphenylene ether (hereinafter referred to as "M-PPE"). Then, 2 kg of M-PPE, 3 kg of polyethylene terephthalate (PET resin SA-1206 manufactured by Unitika, Ltd.) and 100 g of dinitrodiamine compound (D) - (a) mentioned in Reference Example 1 - (i) were again mixed by Henschel mixer and pelletized at 270°-300° C. by a twin-screw extruder. The resulting pellet was vacuum dried at 130° C. for 3-4 hours and then a test piece was made therefrom by injection molding. The test piece was cut by microtome and subjected to etching with carbon tetrachloride and particle diameter of dispersed particles in polyphenylene ether phase was observed by a scanning electron microscope to find that the polyphenylene ether phase was finely dispersed in less than about 1 μ. It was further observed that when the molded product was dipped in chloroform at room temperature for 30 minutes, it showed no change.

COMPARATIVE EXAMPLE 1

Example 1 was repeated except that the dinitrodiamine compound was not used. Dispersion state of polyphenylene ether phase and polyethylene terephthalate phase was inferior and aggromerates of about 10 μ or more of polyphenylene ether phase were seen. When the molded test piece was dipped in chloroform, it swelled and a part of the resin was dissolved out.

It can be seen from comparison between Example 1 and Comparative Example 1 that the composition of the present invention was superior in solvent resistance and compatibility between polyphenylene ether and thermoplastic polyester was markedly improved.

REFERENCE EXAMPLE 2

To 5 kg of poly-2,6-dimethylphenylene ether having an intrinsic viscosity of 0.45 dl/g measured in chloroform of 25° C. were added 100 g of maleic anhydride and 20 g of dicumyl peroxide, followed by mixing by Henschel mixer. The mixture was melt kneaded and pelletized by a twin-screw extruder at 300°-320° C. The product is referred to as "M-PPE(1)".

REFERENCE EXAMPLE 3

Reference Example 2 was repeated except that dicumyl peroxide was not used. The product is referred to as "M-PPE(2)".

REFERENCE EXAMPLE 4

Reference Example 2 was repeated except that glycidyl methacrylate was used in place of maleic anhydride. The product is referred to as "GMA-PPE".

EXAMPLES 2-13

The compound comprising the dinitrodiamine mentioned in Reference Example 1, the modified polyphenylene ether mentioned in Reference Examples 2-6, polyphenylene ether which was used in Reference Example 2, but unmodified (referred to as "PPE"), and the thermoplastic polyester and the rubber-like polymer shown in Table 3 were melt kneaded at the mixing ratio as shown in Table 3 by a twin-screw extruder at 250°-300° C. to obtain pellet.

Then, the pellet was injection molded to obtain the given test piece and properties were measured. The results are shown in Table 3.

COMPARATIVE EXAMPLES 2 AND 3

Examples 2 and 3 were repeated except that the compounds comprising dinitrodiamines were not used. The results are shown in Table 3.

TABLE 3

| | Composition | | | | | | | | Izod impact strength | H.D.T. |
|---|---|---|---|---|---|---|---|---|---|---|
| | Polyphenylene ether resins (A) | | Thermoplastic polyesters (B) *1 | | Dinitrodiamine compounds (D) | | Rubber-like polymers (C) *2 | | (23° C., notched) | (4.6 kg/cm²) |
| | Kind | Amount (part by weight) | Kind | Amount (part by weight) | Kind | Amount (part by weight) | Kind | Amount (Part by weight) | kg · cm/cm | °C. |
| Example 2 | PPE | 30 | PET | 70 | b | 1.5 | SBS | 15 | 40 | 153 |
| Example 3 | M-PPE(1) | 45 | PET | 55 | c | 2.0 | SEBS | 10 | 35 | 170 |
| Example 4 | M-PPE(2) | 50 | PET | 50 | d | 1.0 | St-EPR | 20 | 54 | 162 |
| Example 5 | GMA-PPE | 35 | PET | 65 | e | 3.0 | M-SEBS | 13 | 38 | 158 |
| Example 6 | T-PPE | 60 | PET | 40 | f | 2.5 | MEP | 25 | 60 | 150 |
| Example 7 | M-PPE(1) | 40 | PET | 60 | f | 2.0 | SEP | 16 | 50 | 156 |
| Example 8 | PPE | 70 | PET | 30 | g | 1.0 | EMGMA | 15 | 33 | 178 |
| Example 9 | M-PPE(1) | 45 | PBT | 55 | h | 1.5 | EPR | 13 | 55 | 163 |
| Example 10 | M-PPE(2) | 55 | PBT | 45 | i | 3.0 | SEP | 10 | 42 | 170 |
| Example 11 | GMA-PPE | 65 | PBT | 35 | j | 2.0 | GMA-EPR | 15 | 48 | 168 |
| Example 12 | PPE | 30 | PBT | 70 | k | 1.0 | SEBS | 20 | 50 | 155 |
| Example 13 | M-PPE(1) | 70 | PBT | 30 | l | 2.5 | MEP/SEP | 7/8 | 40 | 175 |
| Comparative Example 2 | PPE | 30 | PET | 70 | none | — | SBS | 15 | 2.9 | 143 |
| Comparative Example 3 | M-PPE(1) | 45 | PBT | 55 | none | — | EPR | 13 | 3.1 | 160 |

*1 PBT: Polybutylene terephthalate having an intrinsic viscosity of 1.25 dl/g
PET: Polyethylene terephthalate having an intrinsic viscosity of 1.00 dl/g
Note *2
M-SEBS: Maleic anhydride-modified, hydrogenated styrene-butadiene-styrene block copolymer (KRATON ® FG-1901X manufactured by Shell Chemical Co.)
SEBS: Hydrogenated styrene-butadiene-styrene block copolymer (KRATON ® G-1650 manufactured by Shell Chemical Co.)
EMGMA: Ethylene-methacrylate-glycidyl methacrylate copolymer (ethylene/methacrylate/glycidyl methacrylate = 56.5/42/1.5 wt %)
SEP: Hydrogenated styrene-isoprene block copolymer (KRATON ® G-1701X manufactured by Shell Chemical Co.)
SBS: Styrene-butadiene-styrene block copolymer (CARIFLEX ® TR-1101 manufactured by Shell Chemical Co.)
GMA-EPR: Glycidyl methacrylate-modified ethylene-propylene copolymer (EPR: ESPRENE ® E-120P manufactured by Sumitomo Chemical Co. Ltd., grafting rate of glycidyl methacrylate: 0.7 wt %)
St-EPR: Styrene-modified (grafted) ethylene-propylene copolymer (EPR: ESPRENE ® E-120P manufactured by Sumitomo Chemical Co., Ltd., styrene/ethylene-propylene copolymer = 40/100 wt %)
MEP: Maleic anhydride-modified ethylene-propylene copolymer (EP: ESPRENE ® E-120P manufactured by Sumitomo Chemical Co., Ltd., grafting rate of maleic anhydride: 1.4 wt %)

REFERENCE EXAMPLE 5

Reference Example 3 was repeated except that glutaric acid was used in place of maleic anhydride. The product is referred to as "G-PPE".

REFERENCE EXAMPLE 6

To 5 kg of poly-2,6-dimethylphenylene ether was added 20 liters of xylene and was further added 500 g of anhydrous trimellitic acid chloride. The mixture was kept for 4 hours at refluxing temperature of xylene with stirring. After cooling, the reaction mixture was poured in 40 liters of methanol to precipitate modified polyphenylene ether, and then the precipitates was filtrated and dried. The product is referred to as "T-PPE".

The present invention provides a composition improved in compatibility between thermoplastic polyester and polyphenylene ether and excellent in processability, solvent resistance and impact strength. Thus, the present composition has a wide variety of uses.

This novel composition can be easily processed into shaped articles, sheets, films and the like by methods employed for thermoplastic resins such as injection molding and extrusion molding. These products are excellent in impact resistance, heat resistance, solvent resistance and processability. This composition is especially effective for injection molding.

We claim:

1. A resin composition which comprises:
   100 parts by weight of a composition comprising
   (A) 5-95% by weight of a polyphenylene ether resin and (B) 95–5% by weight of a thermoplastic polyester and 0.01–10 parts by weight, based on said composition comprising (A) and (B), of (D) a compound comprising a dinitrodiamine represented by the formula (I):

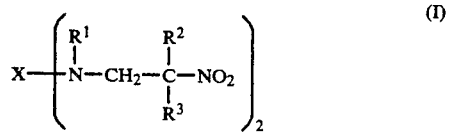

wherein X represents a divalent chain aliphatic, cycloaliphatic or aromatic group which may contain halogen or oxygen, $R^1$ represents a hydrogen atom, a chain aliphatic group, a cycloaliphatic group or an aromatic group and when X and $R^1$ are both chain aliphatic groups, the nitrogen atoms may further link through $R^1$ to each other, $R^2$ and $R^3$ each independently represents a hydrogen atom or an alkyl group of 1–12 carbon atoms and $R^2$ and $R^3$ may link to each other to form a ring.

2. A resin composition according to claim 1 which additionally contains (C) a rubberlike polymer in an amount of 100 parts by weight or less based on 100 parts by weight of the composition comprising (A) and (B).

3. A resin composition according to claim 1, wherein the polyphenylene ether resin (A) is at least one resin selected from the group consisting of a polyphenylene ether, a modified polyphenylene ether, a composition containing a polyphenylene ether and a composition containing a modified polyphenylene ether.

4. A resin composition according to claim 3, wherein the modified polyphenylene ether is obtained by modifying a polyphenylene ether with a polyfunctional compound (E) having in its molecule at least one group selected from the group consisting of a carboxylic acid group, an acid anhydride group, an acid amide group, an imide group, a carboxylic acid ester group, an epoxy group, an amino group and a hydroxyl group in the presence or absence of a radical initiator.

5. A resin composition according to claim 4, wherein the polyfunctional compound (E) is a compound (F) having in its molecule both (a) a carbon-carbon double bond or a carbon-carbon triple bond and (b) at least one group selected from the group consisting of a carboxylic acid group, an acid anhydride group, an acid amide group, an imide group, a carboxylic acid ester group, an epoxy group, an amino group and a hydroxyl group.

6. A resin composition according to claim 4, wherein the polyfunctional compound (E) is a compound (G) which is an aliphatic carboxylic acid, acid ester or acid amide represented by the formula:

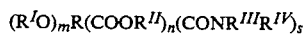

wherein R represents a straight chain or branched chain aliphatic saturated hydrocarbon residue of 2–20 carbon atoms, $R^I$ each independently represent a hydrogen atom or an alkyl, aryl, acyl or carbonyldioxy group of 1–10 carbon atoms, $R^{II}$ each independently represents a hydrogen atom or an alkyl or aryl group of 1–20 carbon atoms, $R^{III}$ and $R^{IV}$ each independently represents a hydrogen atom or an alkyl or aryl group of 1–10 carbon atoms and m, n, and s each represents 0 or an integer of 1 or more with $m+n+s \geq 2$, or a derivative thereof.

7. A resin composition according to claim 4, wherein the polyfunctional compound (E) is a compound (H) which has in its molecule both (a) an acid halide group and (b) at least one functional group selected from the group consisting of a carboxylic acid group, an acid anhydride group, a carboxylic acid ester group and an acid amide group.

8. A resin composition according to claim 3, wherein the modified polyphenylene ether is obtained by modifying a polyphenylene ether with at least one epoxy compound (J) selected from the group consisting of a compound having in its molecule an oxirane ring and a condensation polymer of a dihydric phenol and epichlorohydrin, in the presence or absence of a radical initiator.

9. A resin composition according to claim 3, wherein the modified polyphenylene ether is obtained by modifying a polyphenylene ether with an organosilane compound (K) having in its molecule simultaneously (a) at least one silicon atom which bonds to carbon atom through oxygen atom, (b) a carbon-carbon double bond or a carbon-carbon triple bond and (c) at least one functional group selected from the group consisting of an amino group, a mercapto group, a carboxylic acid group, an acid anhydride group, an acid amide group, a carboxylic acid ester group, an imide group and a hydroxyl group, in the presence or absence of a radical initiator.

10. A resin composition according to claim 1 which additionally contains (M) an aromatic vinyl polymer, a copolymer of an aromatic vinyl compound with another monomer or a rubber-modified aromatic vinyl polymer.

* * * * *